(12) United States Patent
Yan et al.

(10) Patent No.: US 11,911,062 B2
(45) Date of Patent: Feb. 27, 2024

(54) TRANSDUCER FOR ULTRASONIC SCALPEL

(71) Applicant: INNOLCON MEDICAL TECHNOLOGY (SUZHOU) CO., LTD., Suzhou (CN)

(72) Inventors: Zhongyu Yan, Irvine, CA (US); Lei Wang, Suzhou (CN); Wei Luo, Suzhou (CN)

(73) Assignee: INNOLCON MEDICAL TECHNOLOGY (SUZHOU) CO., LTD., Suzhou (CN)

( * ) Notice: Subject to any disclaimer, the term of this patent is extended or adjusted under 35 U.S.C. 154(b) by 1015 days.

(21) Appl. No.: 16/649,069

(22) PCT Filed: Jul. 2, 2018

(86) PCT No.: PCT/CN2018/093988
§ 371 (c)(1),
(2) Date: Mar. 19, 2020

(87) PCT Pub. No.: WO2019/076085
PCT Pub. Date: Apr. 25, 2019

(65) Prior Publication Data
US 2020/0275947 A1    Sep. 3, 2020

(30) Foreign Application Priority Data
Oct. 19, 2017    (CN) .......................... 201710979896.6

(51) Int. Cl.
*B06B 1/06* (2006.01)
*A61B 17/32* (2006.01)
*H02N 2/00* (2006.01)
*H04R 17/00* (2006.01)

(52) U.S. Cl.
CPC ........ *A61B 17/320068* (2013.01); *B06B 1/06* (2013.01); *H02N 2/0025* (2013.01); *H04R 17/005* (2013.01); *A61B 2017/320075* (2017.08)

(58) Field of Classification Search
CPC ............................... B06B 1/06; H02N 2/0025
See application file for complete search history.

(56) References Cited

U.S. PATENT DOCUMENTS

| | | |
|---|---|---|
| 5,151,099 A | 9/1992 | Young et al. |
| 2009/0228032 A1 | 9/2009 | Babaev |
| 2012/0293044 A1 | 11/2012 | Bromfield |
| 2013/0116717 A1 | 5/2013 | Balek et al. |
| 2014/0005702 A1* | 1/2014 | Timm .................... A61B 17/29 606/169 |

(Continued)

FOREIGN PATENT DOCUMENTS

| | | |
|---|---|---|
| CA | 2692273 A1 | 1/2009 |
| CN | 201870672 U | 6/2011 |

(Continued)

*Primary Examiner* — Bryan P Gordon
(74) *Attorney, Agent, or Firm* — Seed IP Law Group LLP

(57) ABSTRACT

A transducer for an ultrasonic scalpel, which comprises, from distal end to proximal end of a connecting feature, a fixing feature, a horn, a piezoelectric converting body, a rear-end ring, and a connecting member. By following a design principle of constraints in the parameter relationships between the piezoelectric converting body and the horn in the transducer, a transducer having both appropriate gain and stable performance can be achieved.

14 Claims, 2 Drawing Sheets

(56) References Cited

U.S. PATENT DOCUMENTS

2016/0325311 A1* 11/2016 Vaitekunas ...... A61B 17/22012
2017/0007852 A1*  1/2017 Isola ......................... A61L 2/07
2018/0014846 A1*  1/2018 Rhee ......................... B06B 3/00
2018/0318878 A1* 11/2018 Akagane ................. A61B 17/29
2019/0090900 A1*  3/2019 Rhee .............. A61B 17/320068

FOREIGN PATENT DOCUMENTS

| CN | 106552760 A | 4/2017 |
| CN | 107595367 A | 1/2018 |
| WO | 2017/126032 A1 | 7/2017 |

* cited by examiner

TRANSDUCER FOR ULTRASONIC SCALPEL

BACKGROUND

Technical Field

This invention relates to the field of medical devices, in particular to an ultrasonic scalpel transducer.

Description of the Related Art

Ultrasonic scalpel large-scale applications have had more than 20 years of history. Comparing to other surgical methods, ultrasonic scalpel has advantages of producing less smoke, clearer surgical view field, smaller thermal damage; it combines multiple functions of tissue cutting, coagulation and dissection in one instrument, and is able to precisely control the cutting and coagulation area; no electrical damage; rapid ultrasonic oscillation has a self-cleaning effect, which reduces the sticking of blade with tissue.

Ultrasonic scalpel can be used for laparoscopic and endoscopic surgery, and for open surgery as well; can be used in combination with other surgical instruments, such as traditional mechanical scalpels and electric knifes, and can be used alone as well, because it combines multifunction of grasping, cutting, dissection and coagulation in one instrument. For different operations, suitable hand pieces are needed for easy operation and more stable performance.

For the safety purpose, the doctor's hand-held ultrasonic scalpel device cannot overheat during the working process, so it is necessary to improve the efficiency of the ultrasonic scalpel, to make itself consume very little energy. In order to achieve the above, it is necessary to increase the gain of the ultrasonic scalpel system. However, too much high gain will reduce the stability of the system.

BRIEF SUMMARY

Provided is a transducer that improves the gain of the ultrasonic scalpel system but without sacrificing the stability.

In order to solve technical problems, provided is a transducer for an ultrasonic scalpel, which from distal end to proximal end comprises a connecting feature, a fixing feature, a horn, a piezoelectric converting body, a rear-end ring and a connecting member. The total length $Ld$ of the piezoelectric converting body satisfies the following formula: the wavelength in the piezoelectric converting body corresponding to the operating frequency of the transducer is $\lambda$; the horn is provided with two sections for amplitude amplification; the diameters of the front and back ends at the two sections are $Df1$, $Db1$ and $Df2$, $Db2$; the following conditions are satisfied between $Ld$, $\lambda$, $Df1$, $Db1$, $Df2$, and $Db2$:

$$\frac{Ld}{\lambda} = \frac{1}{25} \times \left(\frac{Db1}{Df1} \times \frac{Db2}{Df2}\right)^2 - 1/5 \quad (1)$$

$$2 < \frac{Db1}{Df1} \times \frac{Db2}{Df2} < 4 \quad (2)$$

When $Df2$ and $Db1$ are chosen based on a practical application needs, $Df1$ and $Db2$ are calculated according to formula (2), and then $Ld$ is obtained according to formula (1) and $\lambda$; the calculated result of $Ld$ is adjustable within a range of 10%.

Preferably, the piezoelectric converting body includes 4-8 piezoelectric elements.

Preferably, the piezoelectric converting body is within the proximal half wavelength region.

Preferably, the rear-end ring and the connecting member at the proximal end are made of steel or titanium alloy, and the horn at the distal end is made of aluminum or titanium alloy.

In a preferred solution, the horn includes:

A tapered cone and a stepped portion at the proximal end; the cone includes a front end and a back end, and the front end is connected to the stepped portion; the front end diameter is $Df1$, and the back end diameter is $Db1$;

An enlarged portion in the middle section and the diameter of the enlarged portion is $Db2$;

In the distal section, a tapered arc portion is formed. The arc portion extends to the distal end with a distal rod, and the diameter of the distal rod is $Df2$.

Preferably, the cone body and the stepped portion form a first amplification portion; the enlarged portion and the distal rod form a second amplification portion.

Or another preferred solution, the horn includes:

A tapered cone and a stepped portion at the proximal end; the cone includes a front end and a back end; the front end diameter is $Df1$, and the back end diameter is $Db1$;

An enlarged portion is provided in the middle section, a flange structure is provided on the enlarged portion, and a step connected to the flange structure is provided. An arc is provided at the connection between the enlarged portion and the distal rod. The diameter of the enlarged part connected to the arc part is $Db2$; and the diameter of the distal rod is $Df2$.

Preferably, the cone body and the stepped portion form a first amplification portion; the enlarged portion and the distal rod form a second amplification portion.

Preferably, the core length of the horn is 64-72 mm from the front end surface to the back end surface.

Preferably, the ultrasonic scalpel transducer is a wavelength transducer, specifically the transducer is provided with two longitudinal vibration nodes.

The transducer provided here considers the mechanical and electrical gains of the transducer together, so that the total gain of the hand piece and the stability of the system can be improved at the same time. For the mechanical load to the ultrasonic scalpel, that is, the mechanical impedance generated by clamping the soft tissue, if the mechanical gain, that is, the amplitude amplification calculated by formula (2) is too small, the transducer will become hot due to the large mechanical oscillations in the body. However, if the amplitude amplification from the first amplification portion is too large, the amplitude at the distal end may be suppressed and the output may be unstable. By using two amplification portions and the amplification range limited by formula (2), one can make a transducer suitable for such soft tissue surgical load conditions. According to the mechanical gain, the electrical gain must also be adjusted. Otherwise, the electrical input impedance of the transducer may be very high and sensitive to the load and frequency. Therefore, the size and position of the piezoelectric converting body need to be adjusted accordingly.

DETAILED DESCRIPTION

In order to enable those skilled in the art to better understand the technical schemes of the present invention, the present invention will be further described in detail below with reference to specific embodiments.

In order to meet the appropriate gain, dielectric performance, enough ability to drive tissue cutting and coagulating, and the requirements from circuit drive, the present invention proposes the following design scheme:

A transducer used for an ultrasonic scalpel, which from distal end to proximal end comprises a connecting feature, a fixing feature, a horn, a piezoelectric converting body, a rear-end ring and a connecting member. The total length of the converting body is Ld, and its wavelength corresponding to the operating frequency of the transducer is λ. The horn is provided with two sections for amplitude amplification; the diameters of the front and back ends at the two sections are Df1, Db1 and Df2, Db2; the following conditions are satisfied between Ld, λ, Df1, Db1, Df2, and Db2:

$$\frac{Ld}{\lambda} = \frac{1}{25} \times \left(\frac{Db1}{Df1} \times \frac{Db2}{Df2}\right)^2 - 1/5 \quad (1)$$

$$2 < \frac{Db1}{Df1} \times \frac{Db2}{Df2} < 4 \quad (2)$$

When Df2 and Db1 are chosen based on practical application requirements, Df1 and Db2 are calculated according to formula (2), and then Ld is obtained according to formula (1) and λ; the calculated result of Ld is adjustable within a range of 10%.

As we know, the ultrasonic scalpel system usually consists of three parts, the ultrasonic generator, the hand piece and the instrument aka tool. The connected hand piece and instrument are called hand-held device here. According to the convenience of operation, there are two types of hand-held devices that are more suitable for laparoscopic and open surgery, respectively. The ultrasonic electric generator generates ultrasonic frequency electric signal, to drive the hand piece to vibrate through the connecting cable. The hand piece transmits the ultrasonic vibration to the cutting blade through the waveguide inside the instrument. The blade contacts the tissue to produce cutting and coagulating effects.

The gain of the hand-held device is determined by both the hand piece and the instrument. The transducer is the key ultrasonically functional component of the hand piece, so the gain of the transducer constitutes a part of the system gain. In order to achieve the beneficial effect of optimizing gain and increasing stability, with reference to the drawings, the technical scheme and characteristics of this transducer design are described in detail below.

Figure 1:
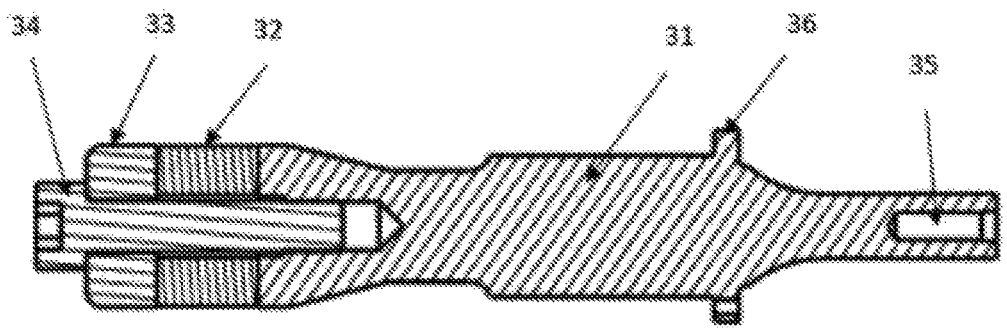
FIG. 1 is a schematic diagram of a transducer provided by Embodiment 1 of the present invention.

According to the calculation from the above formulas, the structure of the transducer is obtained. FIG. 1 is a schematic diagram of a transducer usually used in laparoscopic or endoscopic surgery, including: horn 31, piezoelectric converting body 32, rear-end ring 33, and connecting member 34. On the horn, at the node usually has a protrusion 36, which is similar to the flange design, and is used to fix the hand piece housing. At the distal end is a connecting feature 35, which is used to connect the instrument.

Figure 2:
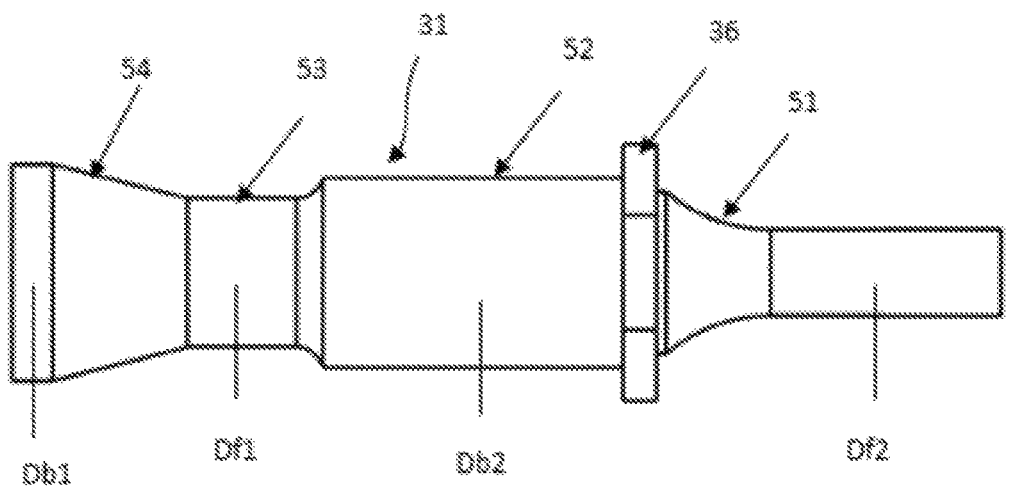
FIG. 2 is a schematic diagram of a horn corresponding to a transducer provided in Embodiment 1 of the present invention.

Based on the above design scheme, in order to meet the reasonable design of different variables in the transducer, provided is a specific structure design of the horn as shown in FIG. 2, which is the horn included in the transducer shown in FIG. 1.

A tapered cone 54 and a stepped portion 53 are provided at the proximal end; the cone 54 includes a front end and a back end, the front end is connected to the stepped portion. The front end diameter is Df1, and the back end diameter is Db1, range 12-19 mm. Preferably, the diameter Df1 of the front end of the cone 54 is 7-14 mm, more preferably 10-11 mm, and most preferably 10 mm. The length of the step 53 is preferably 7-14 mm, more preferably 10 mm. The cone 54 has a length of 7-14 mm. An enlarged portion 52 is provided in the middle section, and the diameter of the enlarged portion 52 is Db2; the diameter of the Db2 is preferably 12-16 mm, and more preferably 14 mm. At the distal end, there is a tapered arc portion 51. The arc portion 51 extends to the distal end with a distal rod. The diameter of the distal rod is Df2, which is 5-10 mm. The arc radius is preferably 10-16 mm, and more preferably 12 mm.

Figure 3:
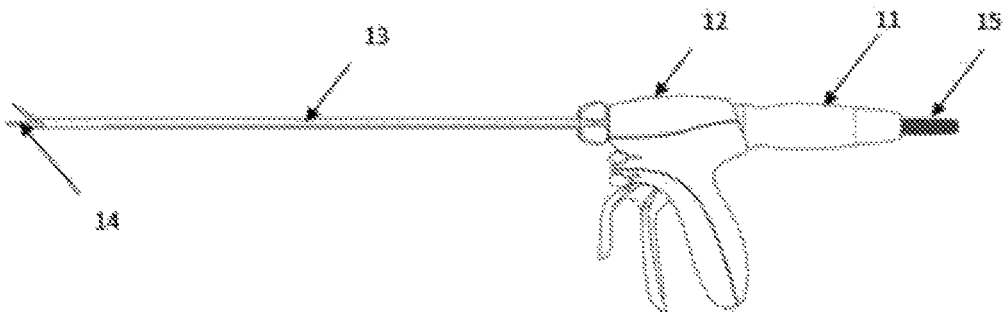
FIG. 3 is a schematic diagram of a hand piece and an instrument used for laparoscopic or open surgery provided in Embodiment 1 of the present invention.

FIG. 3 is a schematic view of a hand piece and an instrument for laparoscopic surgery, including a driving hand piece 11, a transducer disposed inside the housing of the hand piece, an instrument housing 12, a sheath 13, a blade 14 and a connecting cable 15. Through the connecting cable 15 the hand piece 11 is driven by the generator. The hand piece transmits ultrasonic frequency vibration to the blade 14 through the waveguide inside the sheath 13, and the blade 14 contacts the tissue to produce cutting and coagulating effects.

In this embodiment, the operating frequency of the transducer is 53-57 kHz, the corresponding wavelength λ, in the piezoelectric converting body is 88-94 mm, and Ld is 8-15 mm.

Figure 4:
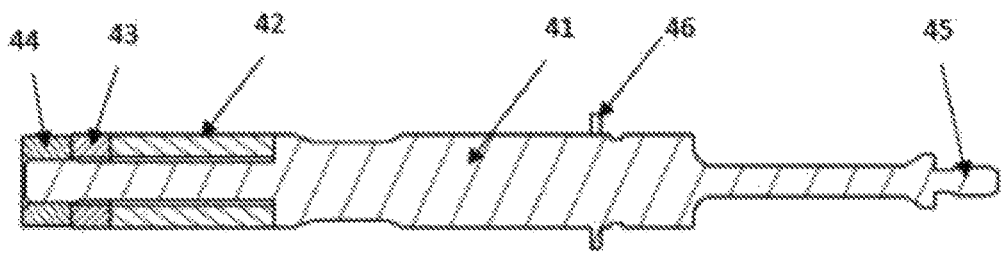
FIG. 4 is a schematic diagram of a transducer provided by Embodiment 2 of the present invention.

FIG. 4 is a schematic diagram of an open surgical transducer, including: a horn 41, a piezoelectric converting body 42, a rear-end ring 43, and a connecting member 44; The protrusion 46, at the vibration node on the horn, has a flange-like design for fixing the hand piece housing; and a connecting feature 45 is provided at the distal end for connecting an instrument.

The diameter of the piezoelectric converting body 42 in the transducer of FIG. 4 is preferably 8.5-11 mm, more preferably 9.5 mm; the total length Ld of the piezoelectric converting body 42 is preferably 12-20 mm, and more preferably 16 mm, and the piezoelectric converting body part is composed of 6-12 pieces of piezoelectric elements, preferably 8 pieces.

Figure 5:
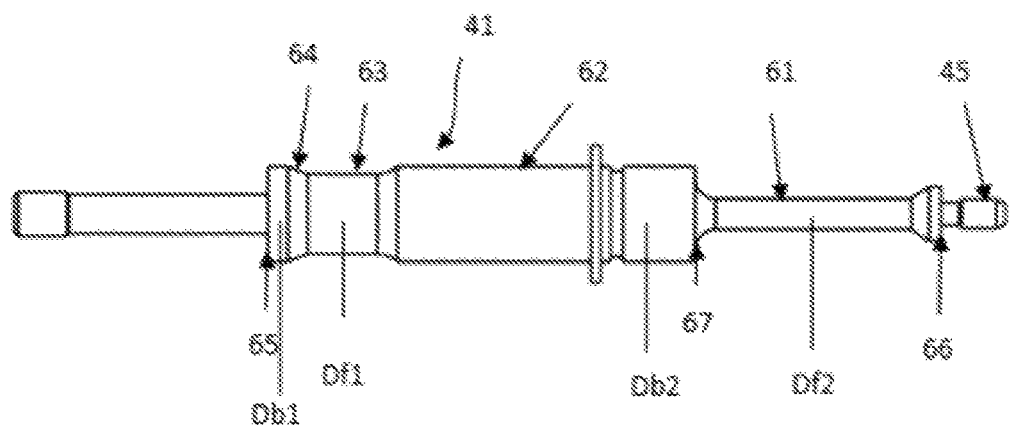
FIG. 5 is a schematic diagram of a horn corresponding to a transducer provided in Embodiment 2 of the present invention.

As shown in FIG. 5, the horn used in the transducer shown in FIG. 4 includes a tapered cone 64 and a stepped portion 63 at the proximal end. The cone 64 includes a front end and a back end. The diameter Db1 of the back end is preferably 8.5-11 mm, more preferably 9.5 mm; and the diameter Df1 of the front end of the cone 64 is preferably 7-9 mm, more preferably 8 mm; the length of the cone 64 is preferably 1-4 mm, more preferably 2 mm; the change in the length of the step 63 will affect the amplification of the first amplitude gain, so in order to better obtain the amplitude of the first amplitude gain, the length of the step 63 in this embodiment is preferably 5-9 mm, more preferably 7 mm.

An enlarged portion 62 is provided in the middle section, a flange structure is provided on the enlarged portion 62, and a step connected to the flange structure is provided. There is an arc portion connecting the enlarged portion and the distal rod, the enlarge portion diameter close to the arc is Db2, preferably 9-12 mm.

The diameter Df2 of the distal rod 61 is preferably 2.6-3.6 mm, more preferably 3.1 mm, and the core length of the horn from the end face 65 to the end face 66 is preferably 64-72 mm, more preferably 68 mm.

Preferably the transducer is a wavelength transducer, specifically, the transducer is provided with two longitudinal vibration nodes.

The piezoelectric converting body is within the proximal end half-wavelength region. If the piezoelectric converting body is outside this region, the electrical gain of the transducer will be reduced, the electrical input impedance will be high, and it will be sensitive to the load and frequency. Therefore, the position of the piezoelectric converting body needs to be maintained. The position of the piezoelectric converting body in the transducer affects the characteristics of the latter.

Figure 6:
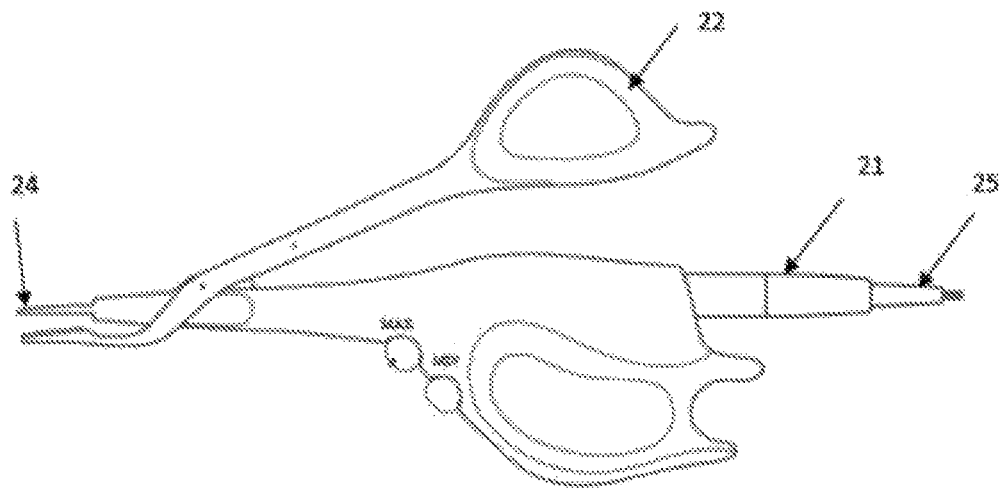
FIG. 6 is a schematic diagram of a hand piece and an instrument used in open surgery provided in Embodiment 2 of the present invention.

FIG. 6 is a schematic diagram of a hand piece and an instrument used in open surgery provided in Embodiment 2 of the present invention. Provided is a hand piece 21, a housing 22, a cable 25, and a blade 24.

In order to further improve the service life and electrical performance of the transducer. Preferably, the rear-end ring and the connecting member at the proximal end of the transducer are made of steel or titanium alloy, and the distal end horn is made of aluminum or titanium alloy.

The above are only preferred embodiments of the present invention. It should be noted that the above preferred embodiments should not be considered as a limitation on the present invention, and the protection scope of the present invention shall be subject to the scope defined by the claims. For those of ordinary skill in the art, without departing from the spirit and scope of the present invention, a number of improvements and modifications can be made, and these improvements and modifications should also be regarded as within the protection scope of the present invention.

The invention claimed is:

1. An ultrasonic scalpel transducer comprising, from distal end to proximal end, a connecting feature, a fixing feature, a horn, a piezoelectric converting body, a rear-end ring, and a connecting member,
wherein a total length of the piezoelectric converting body Ld meets the following constraints:
with respect to an operating frequency of the transducer, a wavelength in the piezoelectric converting body is λ;
the horn has first and second amplification steps;
at the amplification steps, diameters of the horn are Db1 at a proximal end portion, Df1 at a first step section, Db2 at a middle portion, and Df2 at a distal end portion, wherein equations (1) and (2) are defined by:

$$\frac{Ld}{\lambda} = \frac{1}{25} \times \left(\frac{Db1}{Df1} \times \frac{Db2}{Df2}\right)^2 - 1/5 \quad (1)$$

$$2 < \frac{Db1}{Df1} \times \frac{Db2}{Df2} < 4; \quad (2)$$

Df2 and Db1 are determined, Df1 and Db2 are selected according to equation (2), then Ld is calculated according to equation (1) and λ;
wherein the Ld is within 10% of the calculated Ld.

2. The ultrasonic scalpel transducer according to claim 1, wherein the piezoelectric converting body comprises four to eight piezoelectric elements.

3. The ultrasonic scalpel transducer according to claim 2, wherein the piezoelectric converting body is within a half wavelength from the transducer proximal end.

4. The ultrasonic scalpel transducer according to claim 1, wherein the proximal end portion is a proximal end ring adjacent to the piezoelectric converting body wherein the proximal end ring and the connecting member are made of steel or titanium alloy, and the distal end portion is made of aluminum or titanium alloy.

5. The ultrasonic scalpel transducer according to claim 1, wherein the horn comprises:
a tapered cone between the proximal end portion and the first step section; and
a tapered arc section between the middle portion and distal end portion.

6. The ultrasonic scalpel transducer according to claim 5, wherein a first amplification segment is formed by the tapered cone and the first step section, and wherein a second amplification segment is formed by the middle portion and the distal end portion.

7. The ultrasonic scalpel transducer according to claim 1, wherein the horn comprises:
a tapered cone between the proximal portion and the first step section, section wherein a first end of the tapered cone has a diameter of Db1, and a second end of the tapered cone has a diameter of Df1,
wherein the middle portion has a flange structure configured to couple the ultrasonic scalpel transducer to a hand piece housing
wherein the middle portion is connected with the distal end portion by an arc portion.

8. The ultrasonic scalpel transducer according to claim 7, wherein a first amplification segment is formed by the tapered cone and the first step section, and wherein a second amplification segment is formed by the middle portion and the distal end portion.

9. The ultrasonic scalpel transducer according to claim 7, wherein a length of the horn from a first face to a second face is 64-72 mm.

10. The ultrasonic scalpel transducer according to claim 1 wherein the transducer is a whole wavelength transducer.

11. The ultrasonic scalpel transducer according to claim 10, wherein the transducer is configured to operate with two longitudinal vibration nodes.

12. The ultrasonic scalpel transducer according to claim 1, wherein the Ld is equal to the calculated Ld.

13. A handpiece comprising:
a housing; and
the ultrasonic scalpel transducer according to claim 1 located in the housing.

14. The handpiece according to claim 13, wherein the ultrasonic scalpel transducer includes a flange on the middle portion that couples the ultrasonic scalpel transducer to the housing.

* * * * *

UNITED STATES PATENT AND TRADEMARK OFFICE
CERTIFICATE OF CORRECTION

PATENT NO. : 11,911,062 B2
APPLICATION NO. : 16/649069
DATED : February 27, 2024
INVENTOR(S) : Zhongyu Yan et al.

Page 1 of 1

It is certified that error appears in the above-identified patent and that said Letters Patent is hereby corrected as shown below:

In the Claims

Column 5, Claim 1, Line 50:
"scalpel transducer comprising," should read: --scalpel transducer, comprising,--

Column 5, Claim 1, Line 58:
"amplification steps;" should read: --amplification steps,--.

Column 6, Claim 1, Line 6:
"Dbl" should read: --Db1--.

Column 6, Claim 1, Line 8:
"$\lambda$;" should read: --$\lambda$,--.

Column 6, Claim 3, Line 14:
"from the transducer proximal" should read: --from the proximal--.

Column 6, Claim 4, Line 17:
"converting body wherein" should read: --converting body, wherein--.

Column 6, Claim 7, Line 41:
"housing" should read: --housing,--.

Signed and Sealed this
Eighteenth Day of February, 2025

Coke Morgan Stewart
*Acting Director of the United States Patent and Trademark Office*